(12) United States Patent
Jackson (10) Patent No.: US 8,523,913 B2
(45) Date of Patent: Sep. 3, 2013

(54) HELICAL GUIDE AND ADVANCEMENT FLANGE WITH BREAK-OFF EXTENSIONS

(76) Inventor: Roger P. Jackson, Prairie Village, KS (US)

( * ) Notice: Subject to any disclaimer, the term of this patent is extended or adjusted under 35 U.S.C. 154(b) by 1854 days.

(21) Appl. No.: 11/268,200

(22) Filed: Nov. 7, 2005

(65) Prior Publication Data
US 2006/0058794 A1 Mar. 16, 2006

Related U.S. Application Data

(63) Continuation-in-part of application No. 11/101,859, filed on Apr. 8, 2005, which is a continuation-in-part of application No. 10/831,919, filed on Apr. 26, 2004, now Pat. No. 8,273,109, which is a continuation-in-part of application No. 10/236,123, filed on Sep. 6, 2002, now Pat. No. 6,726,689.

(60) Provisional application No. 60/627,000, filed on Nov. 10, 2004.

(51) Int. Cl.
*A61B 17/70* (2006.01)

(52) U.S. Cl.
USPC ........................................................ 606/264

(58) Field of Classification Search
USPC ............... 606/246, 264–267, 270, 272, 273, 606/275, 278, 279, 300, 301, 305, 306, 308; 411/2, 3, 5, 393; 403/362
See application file for complete search history.

(56) References Cited

U.S. PATENT DOCUMENTS

| | | | |
|---|---|---|---|
| 3,640,416 | A | 2/1972 | Temple |
| 4,373,754 | A | 2/1983 | Bollfrass et al. |
| 4,600,224 | A | 7/1986 | Blose |
| 4,703,954 | A | 11/1987 | Ortloff et al. |
| 4,707,001 | A | 11/1987 | Johnson |
| 4,850,775 | A | 7/1989 | Lee |
| 5,005,562 | A | 4/1991 | Cotrel |
| 5,022,791 | A | 6/1991 | Isler |
| 5,092,635 | A | 3/1992 | DeLange et al. |
| 5,129,388 | A | 7/1992 | Vignaud et al. |
| 5,154,719 | A | 10/1992 | Cotrel |

(Continued)

FOREIGN PATENT DOCUMENTS

| | | |
|---|---|---|
| DE | 4425392 | 11/1995 |
| DE | 19509331 | 9/1996 |

(Continued)

OTHER PUBLICATIONS

Translation of Shafer (DE 298 10 798 U1), Schreiber Translations, Inc., May 2010.*

(Continued)

*Primary Examiner* — Pedro Philogene
*Assistant Examiner* — David Comstock
(74) *Attorney, Agent, or Firm* — John C. McMahon (57) ABSTRACT

A spinal fixation device combines an open-headed anchor member, such as a bone screw or a hook with spaced apart arms forming a rod receiving channel. The arms have break-off arm extensions that are broken-off or separated after the rod is clamped. The closure and inner surfaces of the arms and tabs have mating helical anti-splay guide and advancement flanges formed thereon which radially interlock and mechanically cooperate to prevent splaying the arms and extensions as the closure is advanced into the rod receiving channel.

18 Claims, 4 Drawing Sheets

(56) References Cited

U.S. PATENT DOCUMENTS

| | | |
|---|---|---|
| 5,176,483 A | 1/1993 | Baumann et al. |
| 5,217,497 A | 6/1993 | Mehdian |
| 5,275,601 A | 1/1994 | Gogolewski et al. |
| 5,321,901 A | 6/1994 | Kelly |
| 5,358,289 A | 10/1994 | Banker et al. |
| 5,427,418 A | 6/1995 | Watts |
| 5,545,165 A | 8/1996 | Biedermann et al. |
| 5,562,663 A | 10/1996 | Wisnewski et al. |
| 5,601,553 A | 2/1997 | Trebing et al. |
| 5,607,304 A | 3/1997 | Bailey et al. |
| 5,641,256 A | 6/1997 | Gundy |
| 5,643,261 A | 7/1997 | Schafer et al. |
| 5,662,652 A | 9/1997 | Schafer et al. |
| 5,683,390 A | 11/1997 | Metz-Stavenhagen et al. |
| 5,697,929 A | 12/1997 | Mellinger |
| 5,713,898 A | 2/1998 | Stucker et al. |
| 5,725,527 A | 3/1998 | Biedermann et al. |
| 5,733,286 A | 3/1998 | Errico et al. |
| 5,738,685 A | 4/1998 | Halm et al. |
| 5,741,254 A | 4/1998 | Henry et al. |
| 5,782,833 A | 7/1998 | Haider |
| 5,800,547 A | 9/1998 | Schafer et al. |
| 5,944,465 A | 8/1999 | Janitzki |
| 6,001,098 A | 12/1999 | Metz-Stavenhagen et al. |
| 6,004,349 A | 12/1999 | Jackson |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,102,913 A | 8/2000 | Jackson |
| 6,117,137 A | 9/2000 | Halm et al. |
| 6,143,032 A | 11/2000 | Schafer et al. |
| 6,235,034 B1 | 5/2001 | Bray |
| 6,254,146 B1 | 7/2001 | Church |
| 6,296,642 B1 | 10/2001 | Morrison et al. |
| 6,315,564 B1 | 11/2001 | Levisman |
| 6,485,492 B1 | 11/2002 | Halm et al. |
| 6,540,749 B2 | 4/2003 | Schafer et al. |
| 6,551,323 B2 | 4/2003 | Doubler et al. |
| 6,726,689 B2 | 4/2004 | Jackson |
| 6,740,086 B2 * | 5/2004 | Richelsoph ................... 606/60 |
| 6,740,089 B2 | 5/2004 | Haider |
| 2004/0162560 A1 | 8/2004 | Raynor et al. |

FOREIGN PATENT DOCUMENTS

| | | |
|---|---|---|
| DE | 29810798 | 12/1999 |
| DE | 19951145 | 5/2001 |
| WO | WO92-03100 | 5/1992 |
| WO | WO94/26191 | 11/1994 |

OTHER PUBLICATIONS

*Spine*, Lipcott, Williams & Wilkins, Inc. vol. 24, No. 15, p. 1495, Aug. 1, 1999.

Brochure of Tyco/Healthcare/Surgical Dynamics on Spiral Radius 90D, Publication Date: Sep. 2001, pp. 1-8.

* cited by examiner

HELICAL GUIDE AND ADVANCEMENT FLANGE WITH BREAK-OFF EXTENSIONS

CROSS-REFERENCE TO RELATED APPLICATIONS

This application claims the benefit of U.S. Provisional Application No. 60/627,000 filed Nov. 10, 2004 and is a continuation-in-part of U.S. patent application Ser. No. 11/101,859, filed Apr. 8, 2005 which is a continuation-in-part of U.S. patent application Ser. No. 10/831,919 filed Apr. 26, 2004, which is a continuation-in-part of U.S. patent application Ser. No. 10/236,123 filed Sep. 6, 2002, now U.S. Pat. No. 6,726,689, all of which are incorporated herein by reference.

BACKGROUND OF THE INVENTION

The present invention relates to improvements in interlocking or interconnecting helical guide and advancement structures such as helical flanges and, more particularly, to mating helical flange arrangements having an anti-splay lip on one flange and a cooperating and interlocking anti-splay groove on the other flange, the flanges being configured so that when radial loading or engagement occurs, the lip and groove resist splaying of an outer one of the members having one of the cooperating flanges on it. Such flanges with anti-splay contours are particularly advantageous when used in combination with open headed bone screws formed with extended arms or tabs to facilitate the capture and reduction of spinal fixation rods, after which the arm extensions or tabs are broken off at weakened areas to form a low profile implant. In particular, in the present invention, the interlocking anti-splay components also are found on the extensions such that force can be applied to a closure and through the closure to a rod positioned between the extensions without splaying the extensions, as the closure holds them in fixed position relative to each other as the closure traverses between the extensions.

Medical implants present a number of problems to both surgeons installing implants and to engineers designing them. It is always desirable to have an implant that is strong and unlikely to fail or break during usage. Further, if one of a set of cooperating components is likely to fail during an implant procedure, it is desirable to control which particular component fails and the manner in which it fails, to avoid injury and to minimize surgery to replace or repair the failed component. It is also desirable for the implant to be as small and lightweight as possible so that it is less intrusive to the patient. These are normally conflicting goals, and often difficult to resolve.

One type of implant presents special problems. In particular, spinal anchor members such as bone screws, hooks, and the like are used in many types of back surgery for repair of problems and deformities of the spine due to injury, disease or congenital defect. For example, spinal bone screws typically have one end that threads into a vertebra and a head at an opposite end. The head is formed with an opening to receive a rod or rod-like member which is then both captured in the channel and locked in the head to prevent relative movement between the various elements subsequent to installation.

A particularly useful type of head for such bone screws is an open head wherein an open, generally U-shaped channel is formed in the head, and the rod is simply laid in the open channel. The channel is then closed with some type of a closure member which engages the walls or arms forming the head and clamps or secures the rod in place within the channel. While the open headed devices are often necessary and preferred for usage, there is a significant problem associated with them. The open headed devices conventionally have two upstanding arms that are on opposite sides of the channel that receives the rod member. The top of the channel is closed by a closure member after the rod member is placed in the channel. Many open headed implants are closed by threaded plugs that screw into threads formed on internal surfaces between the arms, because such configurations have low profiles.

However, such threaded plugs have encountered problems in that they produce radially outward forces that lead to splaying of the arms or at least do not prevent splaying that in turn may lead to loosening of parts and failure of the implant. In order to lock the rod member in place, a significant force must be exerted on the relatively small plug or on a set screw of some type. The forces are required to provide enough torque to insure that the rod member is clamped or locked securely in place relative to the bone screw, so that the rod does not move axially or rotationally therein. This typically requires torques on the order of 100 inch-pounds.

Because open headed implants such as bone screws, hooks and the like are relatively small, the arms that extend upwardly at the head can be spread by radially outwardly directed forces in response to the application of the substantial torquing force required to clamp the rod member. Historically, early closures were simple plugs that were threaded with V-shaped threads and which screwed into mating threads on the inside of each of the arms. The outward flexure of the arms of the head is caused by mutual camming action of the V-shaped threads of the plug and head as advancement of the plug is resisted by clamping engagement with the rod while rotational urging of the plug continues. If the arms are sufficiently spread, they can allow the threads to loosen or disengage and the closure to fail. To counter this, various engineering techniques were applied to the head to increase its resistance to the spreading force. For example, the arms were significantly strengthened by increasing the width of the arms by many times. This is undesirable as it leads to a larger profile implant, which is always undesirable and may limit the working space afforded to the surgeon during implant procedures. Alternatively, external caps were devised which engaged external surfaces of the head. In either case, the unfortunate effect was to substantially increase the bulk, size and profile of the implant, especially when external nuts are used which may take up enough space along the rod so as to leave too little space for all the implants needed.

The radial expansion problem of V-threads has been recognized in various other applications of threaded joints. To overcome this problem, so-called "buttress" threadforms were developed. In a buttress thread, the trailing or thrust surface, also known as the load flank, is oriented perpendicular to the thread axis, while the leading or clearance surface, also known as the stab flank, remains angled. This results in a neutral radial reaction of a threaded receptacle to torque on the threaded member received. However, even buttress threaded closures may fail as such do not structurally resist splaying of the arms.

Development of threadforms proceeded by applicant from buttress threadforms and square threadforms, which have a neutral radial effect on the screw receptacle, to reverse angled threadforms which can positively draw the threads of the receptacle radially inward toward the thread axis when the plug is torqued. In a reverse angle threadform, the trailing side of the external thread is angled toward the thread axis instead of away from the thread axis, as in conventional V-threads. However, outward radial forces on the arms at higher torques can lead to failure and positive mechanical interlocking between the arms and the closure is more desirable and secure. In the present application, such positive interlocking is also provided in vertical extensions of the arms that are eventually broken away and removed.

When rods are implanted in spinal fixation systems, it is often necessary to shape the rod in various ways to properly position vertebrae into which open headed bone screws and related implants have been implanted. The bone screw or implant heads are minimized in length to thereby reduce the profile and minimize the impact of the implanted system on the patient. However, it is often difficult to capture a portion of a straight or curved rod in a short implant head to clamp it within the arms. The extensions allow the arms to extend upwardly and capture the rod therebetween. In this way, the closure can be more easily inserted and rotated to drive the rod downwardly into the head of the implant.

SUMMARY OF THE INVENTION

The present invention provides improved mating guide and advancement flange structure for guiding and advancing an inner member into an outer member in response to relative rotation of the inner and outer member. The structure includes an inner flange on the inner member and an outer flange on the outer member which have complementary contours cooperating on engagement to helically guide the inner member into the outer member by relative rotation about a helical axis and which each radially interlock with opposite structure as the closure is rotated. The inner flange has a radially outward crest and a radially inward root. Conversely, the outer flange has a radially inward crest and a radially outward root.

Each of the inner and outer flange has respective stab flank on a leading side relative the direction of advancement of the inner member into the outer member and a respective load flank on the trailing side of the flange. At least one of the flanks on one member has anti-splay contours forming a lip or bead which projects axially and extends helically therealong, while a corresponding one of the flanks has anti-splay contours forming a complementary groove depressed in an axial direction and positioned to receive the lip. For example, if the lip is formed on the load flank of the inner member at its radial crest, the corresponding groove is formed into the load flank of the outer member near its root.

The lip and groove have radially oppositely facing anti-splay surfaces which are positioned to enable radial engagement or loading of the anti-splay surfaces to resist or prevent splaying of the outer member when the inner member is strongly torqued into the outer member. Preferably, the anti-splay surfaces on the inner member are continuous, whereas the outer member is divided into two parts which are spaced from one another and the anti-splay surfaces thereon are discontinuous.

In a first embodiment of the flange, a lip is formed on the load flank of the inner flange adjacent a crest of the flange. The lip has an anti-splay surface or shoulder which faces inwardly toward coincident helical axes of the inner and outer members which form a joint axis common to both members when so engaged. A corresponding groove is formed into the load flank of the outer flange near the root of the outer flange. The groove has an anti-splay surface or shoulder which faces outwardly away from the joint axis of the members. The anti-splay surfaces of the lip and groove are positioned to mutually engage in a radial direction to resist splaying of the outer member when the inner member is strongly torqued into the outer member.

In the first embodiment, the load flanks of the inner and outer flanges are angled in a slightly "positive" direction; that is, in cross section the load flanks form slightly obtuse angles with the joint axis of the members.

In embodiments wherein the inner and outer flanges have relatively equal cross sections with generally similar shapes, the outer flange tends to be somewhat stronger than the inner flange. As a result of this, when the inner member is very strongly torqued into the outer member, the inner flange is likely to fail before the outer flange.

Although the preceding description of the load flanges describes the load flank of the inner flange as having a lip and the load flank of the outer flange as having a groove, each load flank could be accurately described as having both a lip and a groove. The lip of the inner flange is defined by a radially inward groove while the groove formed in the outer flange defines a radially inward lip. In any case, the lip of one flange enters the groove of the other flange so that the anti-splay surfaces of the flanges are placed in mutually facing relation when the inner member is advanced into the outer member.

The present invention does not limit the anti-splay contours solely to the load flanks of the inner and outer flanges. There are advantages to be gained by forming the lips and grooves on the respective stab flanks of the inner and outer flanges, on leading sides of the flanges as the inner member is advanced into the outer member.

Although it is desirable to form the arms of an open-headed bone screw and related implants as short as possible to result in a low profile implant, it is often difficult to urge a spinal fixation rod into the U-shaped channel between the arms of such a bone screw head. In general, the rods are shaped to determine the shaped of the corrected curvature of the spinal column and are anchored along their length to open-headed bone screws implanted into individual vertebrae. Because of the complex curvature that must be applied to the rods, it is sometimes difficult to reduce a portion of such a rod toward a selected bone screw or implant in a vertebra with a conventionally formed open-head with spaced arms for receiving both the rod and a closure.

The present invention solves this problem by forming arm extensions or tabs on the screw head which are connected to main portions of the arms by weakened break regions. Inner surfaces of the extensions have the helical guide and advancement flanges formed thereon to receive a closure with a flange complementary to the flange of the arms of the screw head. In particular, the extensions have the same anti-splay structure thereon as is found on the arms and the structure on the extensions is aligned with that on the arms so as to provide a continuous helical path for the mating structure on the closure to follow. The extensions or tabs enable the rod to be captured at a greater distance from the anchoring vertebra and urged toward the vertebra by advancement of the closure toward the open head. When the rod has been seated in the rod receiving channel and in the head sufficiently clamped, the tabs can be broken off the main portions of the arms to provide the desired low profile implant. Just as the anti-splay guide and advancement structure on the closure and arms cooperate to prevent splaying of the arms, the anti-splay structure on the extensions cooperates with the cooperating structure on the closure to prevent unwanted splaying of the extension and guides the closure to allow mating with the guide and advancement structure on the arms simply by rotating the closure.

That is, the guide and advancement structure on the closure does not have to be realigned with the cooperating structure on the arms and pressure applied to the rod while between the extensions is continued as the rod passes between the arms.

The anti-splay lip and groove of the flanges of the present invention make the use of such extended arms or tabs possible, even when substantial force must be applied to the rod.

This is a substantial improvement over use of V-threads that may cause outward splaying of the extensions as force is applied to the rod by the closure.

OBJECTS AND ADVANTAGES OF THE INVENTION

The principal objects of the present invention include: providing an improved helical guide and advancement flange structure for guiding and advancing an inner member into an outer member; providing such flange structure for cooperatively radially interlocking between a closure and both implant arms and extensions for such arms as a rod is passed between the extensions to the arms under pressure being applied by rotating or torquing the closure; providing, particularly, improvements in helical guide and advancement flanges incorporating radially loaded lip and groove contours; providing such flange structure wherein the outer member is subject to being splayed in reaction to advancement and torquing of the inner member within the outer member and wherein an inner flange of the inner member and an outer flange of the outer member are particularly configured to cooperate in such a manner as to radially interlock and resist such splaying while allowing rotation and axial advancement; providing such flange structure in which the inner and outer flanges are provided with contours including mutually facing surfaces which radially engage when the inner member is advanced into the outer member to resist splaying of the outer member; providing such flange structure in which anti-splay contours are formed on a trailing load flank of each flange to form an anti-splay lip near a crest region of the inner flange and a cooperating anti-splay groove near a root region of the outer flange; providing such flange structure in which the anti-splay contours are alternatively applied to a leading stab flank of each flange to form an anti-splay lip near a crest region of the inner flange and a cooperating anti-splay groove near a root region of the outer flange; providing such flange structure in which the anti-splay contours are alternatively formed on both the load and stab flanks of each flange to form anti-splay lips near a crest region of the inner flange and cooperating anti-splay grooves near a root region of the outer flange; providing such flange structure which is particularly well adapted for use in surgically implanted structure, such as spinal fixation hardware and, particularly, to receivers and cooperating closures which are used to receive and clamp spinal fixation rods; providing such flange structure which is particularly well adapted for use with open headed bone screws which have extended arms for facilitating the capture and reduction of spinal fixation rods and which are afterwards separated from the screw heads and related implants to provide low profile implants; and providing such improved helical guide and advancement flanges with radially loaded lips which are economical to manufacture, which are strong and effective in use, and which are particularly well adapted for their intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates a helical guide and advancement flange structure in combination with break-off tabs or extension 2 used in conjunction with a medical implant 3 which embodies the present invention.

The flange structure, or flange form, 1 generally includes an inner flange 4 (FIG. 3) extending helically on an inner member 6 and an outer flange 9 extending helically within an outer member 11. The flanges 4 and 9 cooperate to helically guide the inner member 6 into the outer member 11 when the inner member 6 is rotated and advanced into the outer member 11. The inner and outer flanges 4 and 9 have respective anti-splay contours 14 and 16 which cooperate to prevent splaying tendencies of the outer member 11 when the inner member 6 is strongly torqued therein.

In the illustrated embodiment the implant 3 comprises an open-headed bone screw 20 forming the outer member 11 thereon and having a threaded shank 22 adapted for threaded implanting into a bone, such as a vertebra 24. The bone screw 20 has a U-shaped open head 26 formed by spaced apart arms 28 defining a rod receiving channel 30 which is configured to receive a rod 35 and thereafter the rod is clamped or secured within the head 26 to thereby fix the position of the vertebra 24 relative to the rod 35.

The illustrated inner member 6 is a closure 33 which is helically advanced by rotation thereof into the head 26 of the screw 20 and torqued against the rod 35 to clamp the rod within the head 26. Although embodiments of the outer member 11 and inner member 6 are illustrated herein, as the screw head 26 and the closure 33, the flange structure 1 is not intended to be limited to such an application. It is especially noted that the implant 3 may be a hook or other implant structure having a rod receiving channel. Also, while the illustrated screw 20 is shown as a one-piece screw, it is intended that the flange structure 1 be adaptable for use with a polyaxial type of screw.

The inner flange 4 has a load flank 39 on a trailing side relative to a direction of advancement along a helical axis 41 (FIG. 3) and a stab flank 43 on an opposite leading side. Similarly, the outer flange 9 has a load flank 46 on a trailing side and a stab flank 48 on an opposite leading side. The load flanks 39 and 46 may also be referred to as thrust surfaces of the flanges 4 and 6, while the stab flanks 42 and 48 may also be referred to as clearance surfaces. In general, the load flanks 39 and 46 are positively engaged and axially loaded, that is loaded in the direction of the axis 41, when the inner member 6 is advanced into the outer member 11. As relative torque between the inner member 6 and the outer member 11 increases, by engagement with a clamped member such as the rod 35, there is a tendency for the arms 28 of the outer member 11, to splay outward away from the axis 41. In the flange structure 1 of the present invention, the inner and outer anti-splay contours 14 and 16 include respective anti-splay surfaces 52 and 54 which are mutually engaged in a radial direction to radically interconnect, to mechanically interlock and resist such splaying tendencies. Because of the anti-splay configuration of the flange structure 1, the relative torque between the inner and outer members 6 and 11 can be much higher in comparison to conventional V-threads or guide and advancement structures which do not have anti-splay contours, thereby allowing a considerably higher, more positive clamping force to be applied to the closure 33 and the rod 35.

Figure 3:
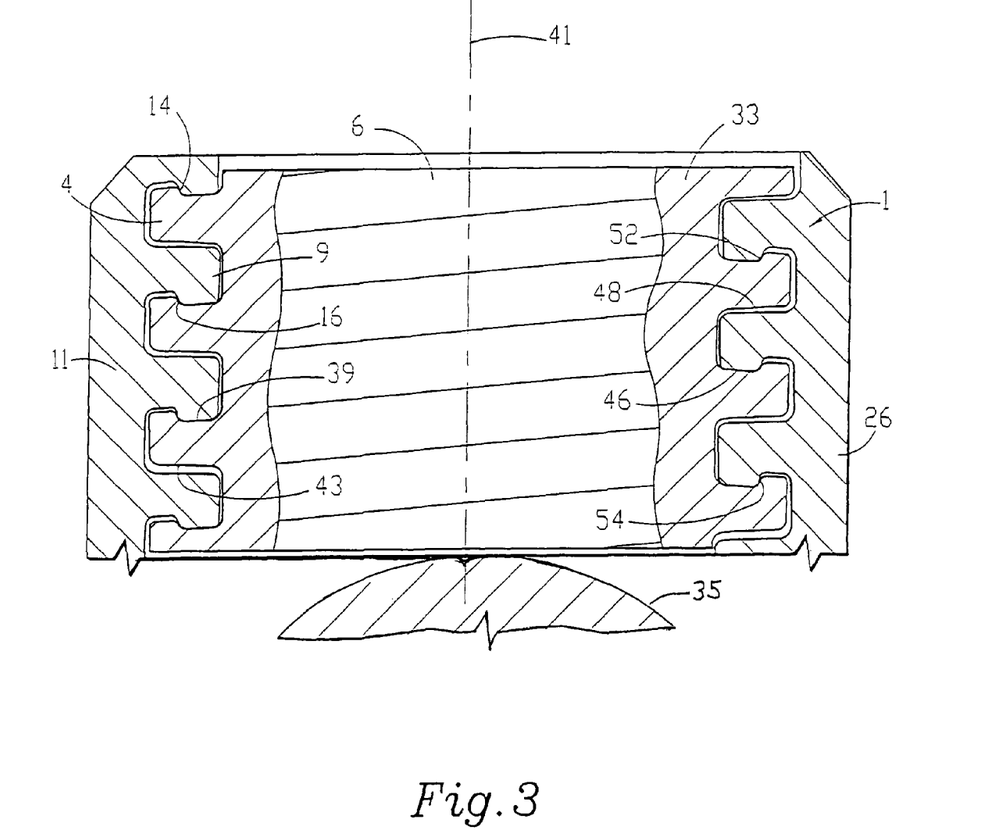
FIG. 3 is a greatly enlarged fragmentary sectional view at a right angle to the view shown in FIG. 2 and illustrates details of the cooperating flanges with the closure strongly torqued into the open headed screw.
Figure 4:
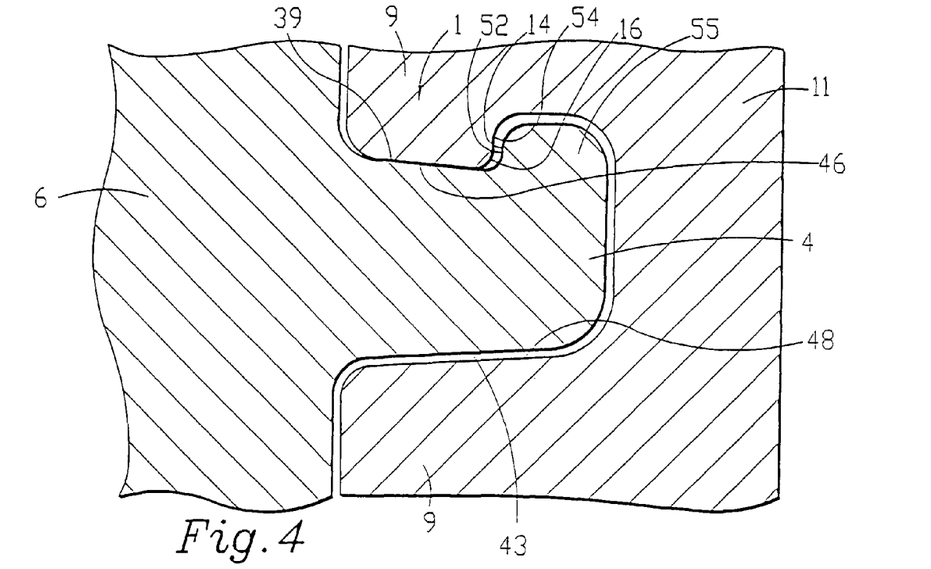
FIG. 4 is a further enlarged fragmentary sectional view of a preferred flange structure according to the present invention and illustrates an anti-splay lip on a load flank of an inner flange and an anti-splay groove on a load flank of an outer flange, the load flanks being parallel and somewhat positive in angular orientation relative to a helical axis.
Figure 5:
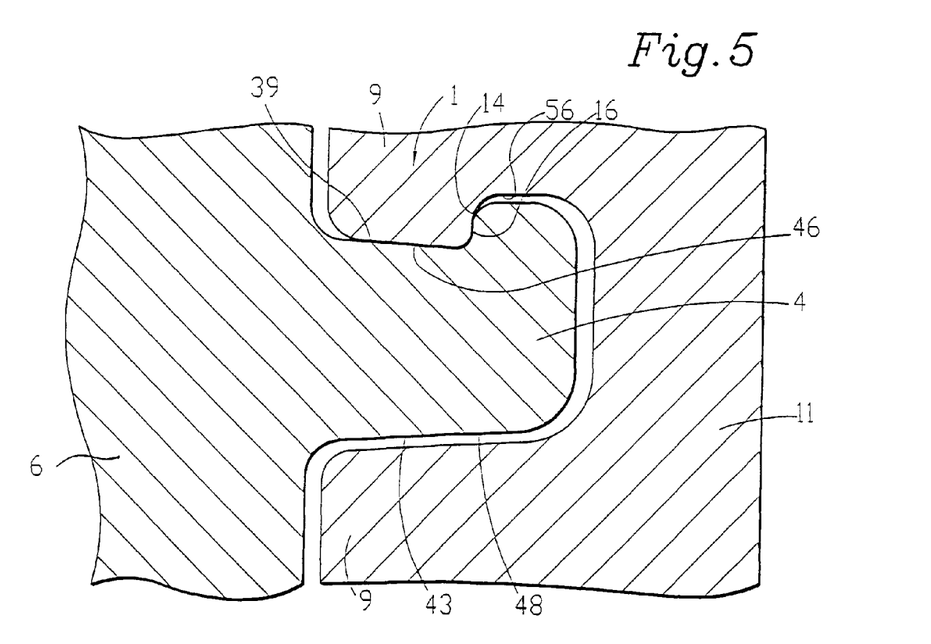
FIG. 5 is a view similar to FIG. 4 and illustrates the preferred flange structure with the inner member strongly torqued within the outer member, thereby mutually engaging the anti-splay surfaces of the lip and groove.

In the illustrated flange structure 1, the inner anti-splay surface 52 is formed by an anti-splay lip 55 extending axially from the load flank 39 of the inner flange 4. Similarly, the outer anti-splay surface 54 is formed by a groove 56 formed into the load flank 46 of the outer flange 9. The lip 55 and groove 56 are shaped in a complementary manner so that the lip 55 is received within the groove 56 when the inner member 6 is advanced into the outer member 11. Although FIGS. 3-5 illustrate a flange structure 1 of a particular configuration and contour, other configurations and contours are contemplated, as disclosed in Ser. No. 10/236,123 referenced above and enclosed herein by reference.

Figures 1, 2:
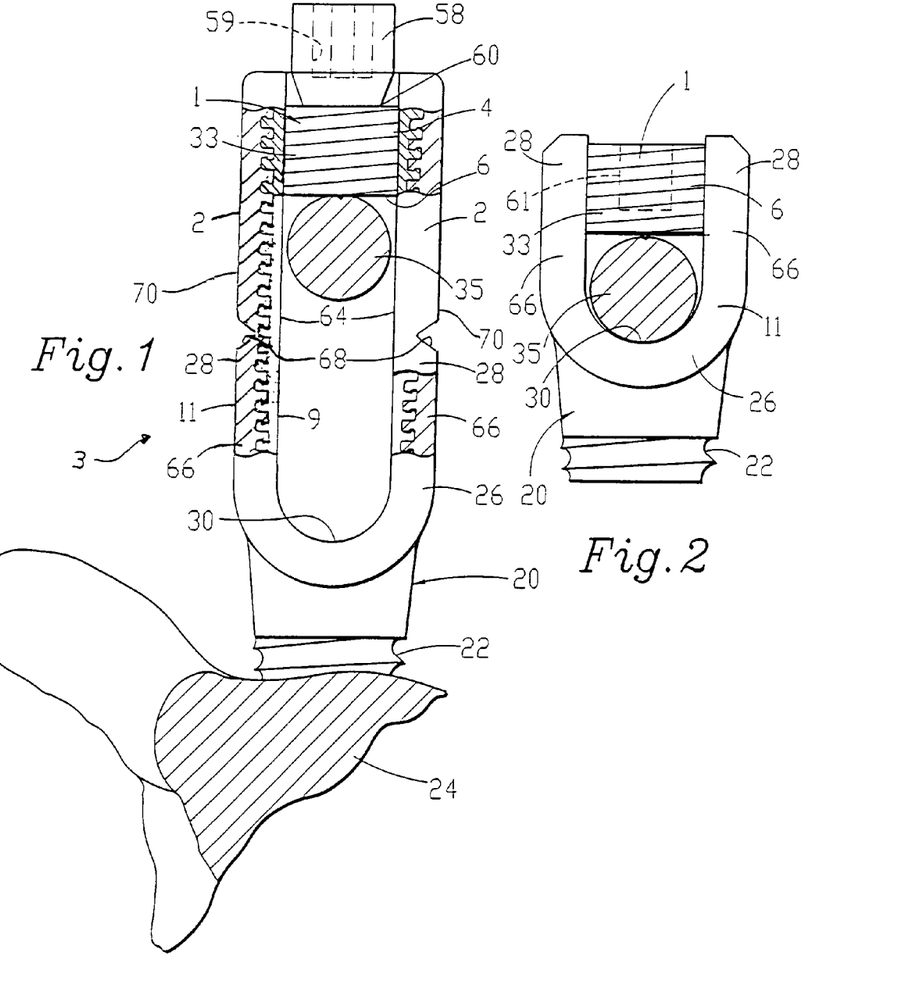
FIG. 1 is an enlarged fragmentary side elevational view of a spinal implant incorporating the helical guide and advancement flange on a closure with a radially loaded lip urging a rod between extensions of arms forming a rod receiving channel on a medical implant bone screw with portions broken away to show detail thereof.
FIG. 2 is a view similar to FIG. 1 and shows the implant with the closure clamping a spinal fixation rod within the channel with the extensions removed.

The closure 33 illustrated in FIG. 1 has a break-off installation head 58 which is provided with a non-round installation socket 59, such as a Torx shaped socket, a hexagonal Allen socket, or the like to receive an appropriately configured installation tool (not shown). The break-off head 58 is joined to the main body of the closure 33 by a weakened region 60 which is configured to limit the torque that can be applied to the head 58, relative to the closure 33, without the head separating from the closure 33 by failure of the weakened region 60. By this means, the head 58 separates from the closure 33 when a selected torque is reached in clamping the rod 35, to thereby provide a low profile implant. Alternatively, the closure 33 could be provided without the break-off head 58. The closure 33 has a non-round socket 61 (FIG. 2) to receive a tool to enable removal of the closure 33 from the screw head 26, if necessary. Such a socket 61 could also be employed for installation of the closure 33 into the screw head 26.

Referring particularly to FIG. 1, the bone screw 20 is provided with the arm tabs on extensions 2 to increase the initial length of the arms 28 and, thus, forming a rod receiving passageway between the extensions 2 and thereby increasing the length of the rod receiving channel 30 by the length of the passageway. The purpose for the lengthened channel 30 is to enable capture of the rod 35 within the channel 30 at a greater distance from the vertebra 24, whereby the rod 35 can be captured by the closure 33 and "reduced" or urged toward a seated position within the channel 30 by advancement of the closure 33. This provides effective leverage in reducing the position of the rod 35 or the vertebra itself. For this purpose, inner surfaces 64 of the tabs 2 are provided with the helical outer flange 9 which extends continuously from main portions 66 of the arms 28 and along the extensions 2 to form a continuous and uniform helical pathway therebetween.

The break-off extensions 2 are connected to the main portions 66 of the arms 28 by reduced or otherwise weakened regions 68. The bone screw 20 illustrated in FIG. 1 shows the weakened regions 68 as regions adjacent V-shaped notches formed into external surfaces 70 of the arms 28 which diminish the thickness of the material forming the arms 28. Alternatively, other shapes or configurations could be employed to form the weakened regions 68. The weakened regions 68 are strong enough to enable the rod 35 to be urged toward its seated position (FIG. 2). However, the extensions 2 can be broken off or separated from the main portions 66 of the arms 28 by pivoting or bending the extensions 2 back and forth about the regions 68 while the main portions 66 are held in place, after the closure 33 has passed between the extensions 2. The resulting low-profile implanted structure is shown in FIG. 2.

Figure 6:
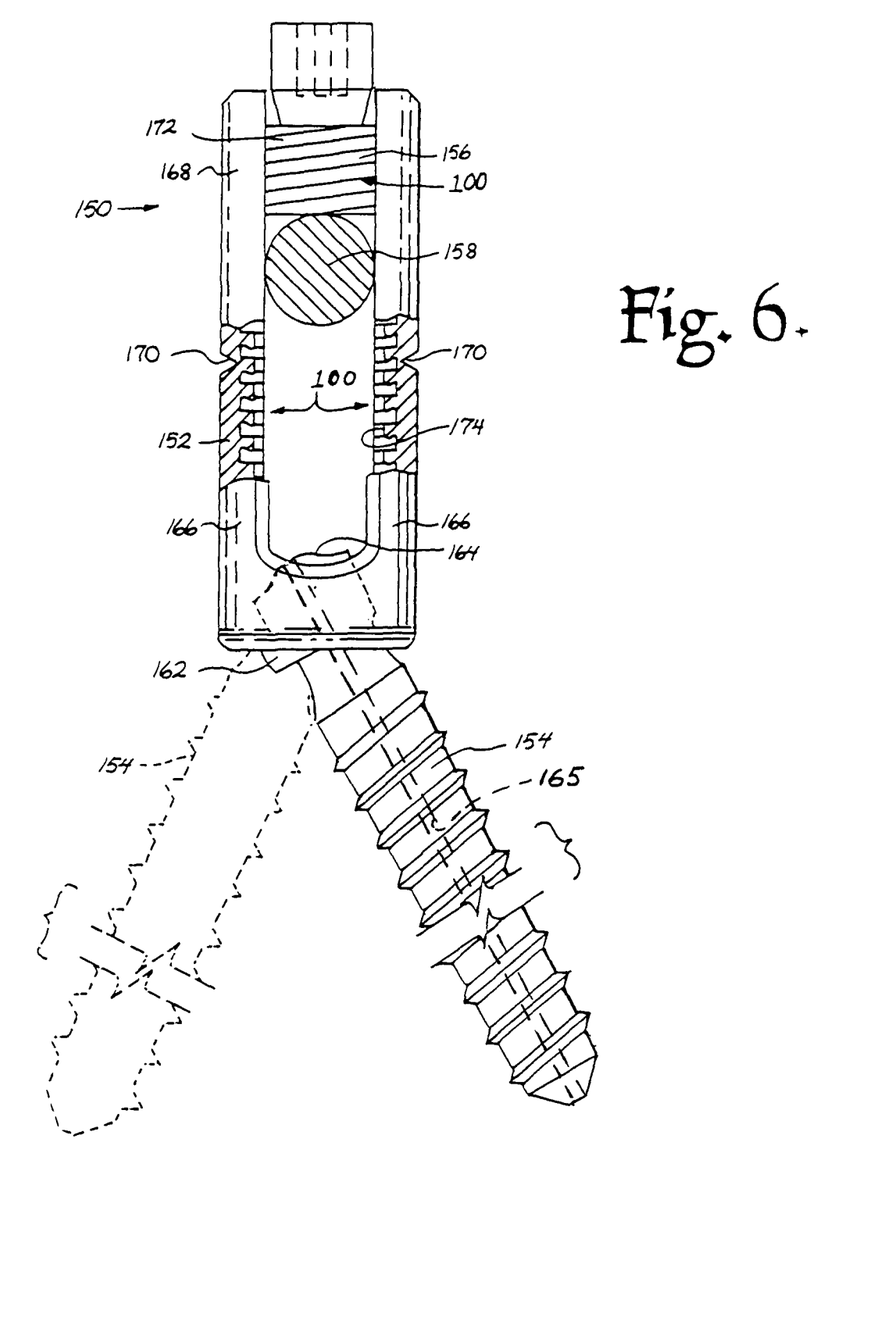
FIG. 6 is an enlarged fragmentary side elevational view of a spinal implant incorporating a helical guide and advancement flange of the present invention and including a polyaxial bone screw.

FIG. 6 illustrates a polyaxial medical implant, generally 150, that incorporates a helical guide and advancement flange structure 100 of the present invention identical to or substantially similar to the structure 1 previously described herein. The illustrated polyaxial implant 150 includes an open headed receiver 152, a threaded shank 154, and a closure 156 that cooperate to fix the position of another implant member, such as a spinal fixation rod 158. The receiver or head 152 is configured internally with a spherical socket (not shown) that receives a shank retainer member 162 having a spherical outer surface. The retainer member 162 is connected to an upper or capture end 164 of the shank 154 and, in cooperation with the receiver socket, enables the shank 154 to be positioned at any desired angle relative to the receiver 152, within a conical range of movement. The shank 154 is secured at the desired angle by engagement of the rod 158 with the upper or capture end 164 when the rod is clamped within the receiver 152 by the closure 156. Shown in phantom in the illustrated embodiment, the threaded shank 154 is cannulated, having a small central bore 165 extending an entire length of the shank body. The bore 165 provides a passage through the shank interior for a length of wire or pin inserted into a vertebra prior to the insertion of the threaded shank body 154, the wire or pin providing a guide for insertion of the shank 154 into the vertebra. Additional information about polyaxial bone screws can be found in U.S. Pat. No. 6,716,214, which is incorporated herein by reference.

The receiver 152 includes spaced apart arms 166 and preferably includes break-off extensions 168 that are separable from the arms 166 by breaking the extensions 168 off at weakened regions 170. The flange structure 100 includes an anti-splay closure guide and advancement flange 172 formed on the closure 156 which cooperates with a discontinuous receiver anti-splay guide and advancement flange 174 formed on inner surfaces of the arms 166 and extensions 168. The flanges 172 and 174 are substantially similar to the flanges 4 and 9 of the implant 3 and benefit from the same variations in configuration as described in connection therewith. The flanges 172 and 174 enable the closure 156 to be advanced into clamping contact with the rod 158 by rotation within the receiver 152. In other respects, the implant 150 is substantially similar to the implant 3.

It is to be understood that while certain forms of the present invention have been illustrated and described herein, it is not to be limited to the specific forms or arrangement of parts described and shown.

What is claimed and desired to be secured by Letters Patent is as follows:

1. A device for securing a rod shaped member and comprising:
   (a) a receiver having spaced apart arms defining a member receiving channel therebetween, said arms having main portions and extended portions connected to said main portions by weakened regions, said main portions and said extended portions of said arms having inner surfaces;
   (b) a closure sized to be received within said channel to clamp the rod shaped member therein and having a body;
   (c) a closure guide and advancement flange extending helically about and along said closure, said closure flange having a closure anti-splay contour with a downwardly facing closure leading surface and a trailing surface; the trailing surface having an inner portion extending outwardly and downwardly from the body and an outer portion that has a surface that is raised above the inner portion;
   (d) a discontinuous receiver guide and advancement flange extending helically about and along said inner surfaces of said main portions and said extended portions of said arms, said receiver flange having a receiver anti-splay contour with an upwardly facing receiver leading surface; the closure trailing surface raised surface being sized and shaped to remain spaced from the receiver guide and advancement flange so as to remain unloaded during use;
   (e) the anti-splay contours of said closure flange and said receiver flange being complementary to mate during rotation of the closure relative to the receiver, while radially interlocking, and thereafter cooperatively to prevent splaying of said arms when said closure is advanced into said receiver; said closure being advanceable against rod shaped member to clamp the member relative to said receiver; said downwardly facing closure leading surface and said upwardly facing receiver leading surface cooperating so as to produce a gap therebetween; and
   (f) said extended portions of said arms guiding the closure into the channel during rotation of the closure into the channel and thereafter being separable from said main portions after said closure clamps the rod shaped member within a portion of said channel defined by said main portions of said arms.

2. The device as set forth in claim 1 wherein:
   (a) said receiver is spinal fixation anchor and said member is a spinal fixation rod.

3. The device as set forth in claim 1 wherein:
   (a) said receiver is an open-headed bone screw adapted for implanting in a vertebra and said member is a spinal fixation rod.

4. The device as set forth in claim 1 wherein:
   (a) said closure anti-splay contour includes a lip extending helically along said closure flange;
   (b) said receiver anti-splay contour includes a groove extending helically along said receiver flange; and
   (c) said lip and said groove cooperate to receive said lip in said groove when said closure is rotated and advanced into said receiver.

5. A device as set forth in claim 1 wherein:
   (a) said closure flange has a closure load flank on a trailing side of said closure flange relative to a clamping direction of movement of said closure within said receiver;
   (b) said closure anti-splay contour includes a lip extending helically along said closure load flank of said closure flange;
   (c) said receiver flange has a receiver load flank on a trailing side of said receiver flange relative to said clamping direction of movement;
   (d) said receiver anti-splay contour includes a groove extending helically along said receiver load flank of said receiver flange; and
   (e) said lip and said groove cooperate to receive said lip in said groove when said closure is rotated and advanced into said receiver.

6. A spinal fixation structure for clamping and anchoring a spinal fixation rod and comprising:
   (a) an open-headed spinal fixation anchor including a pair of spaced apart arms defining a rod receiving channel therebetween, said arms having main portions and extended portions connected to said main portions by weakened regions, said main portions and said extended portions of said arms having inner surfaces;
   (b) a closure having a body and being sized to be received within said channel and adapted to be rotated and advanced into the channel and between the arms to clamp a spinal fixation rod in the channel;
   (c) a closure guide and advancement flange extending helically about and along said closure, said closure flange having a closure anti-splay contour and a downwardly facing closure leading surface and a trailing surface; the trailing surface having an inner portion sloping downwardly and outwardly from the closure body and an outer portion with a raised surface;
   (d) an anchor guide and advancement flange discontinuously extending helically about and along said inner surfaces of said main portions and said extended portions of said arms, said anchor flange having an anchor anti-splay contour and an upwardly facing anchor leading surface complementary to said closure leading surface; the closure trailing surface raised surface being sized and shaped so as to remain spaced from the anchor guide and advancement flange during use;
   (e) an anti-splay gap between said complementary leading surfaces;
   (f) the anti-splay contours of said closure flange and said anchor flange allowing rotation of the closure relative to the anchor while being complementary and radially interlocking so as to cooperate to prevent splaying of said arms when said closure is advanced into said anchor; and
   (g) said extended portions of said arms being separable from said main portions after said closure clamps the rod within a portion of said channel between said main portions of said arms.

7. The device as set forth in claim 6 wherein:
   (a) said anchor is an open-headed bone screw adapted for helical implanting in a vertebra.

8. The device as set forth in claim 6 wherein:
   (a) said closure anti-splay contour includes a lip extending helically along said closure flange;
   (b) said anchor anti-splay contour includes a groove extending helically along said receiver flange; and (c) said lip and said groove cooperate to receive said lip in said groove when said closure is advanced into said anchor.

9. The device as set forth in claim 6 wherein:
(a) said closure flange has a closure load flank on a trailing side of said closure flange relative to a clamping direction of movement of said closure within said anchor;
(b) said closure anti-splay contour includes a lip extending helically along said closure load flank of said closure flange;
(c) said anchor flange has an anchor load flank on a trailing side of said anchor flange relative to said clamping direction of movement;
(d) said anchor anti-splay contour includes a groove extending helically along said anchor load flank of said anchor flange; and
(e) said lip and said groove cooperate to receive said lip in said groove when said closure is advanced into said anchor.

10. A spinal fixation structure for clamping and anchoring a spinal fixation rod and comprising:
(a) a spinal fixation bone screw having an open head including a pair of spaced apart arms defining a rod receiving channel therebetween, said arms having main portions and extended portions connected to said main portions by weakened regions, said main portions and said extended portions of said arms having inner surfaces;
(b) a closure having a body and being sized to be received within said channel to clamp a spinal fixation rod therein;
(c) a closure guide and advancement flange extending helically about and along said closure, said closure flange having a closure anti-splay contour with a downwardly facing closure leading surface and a trailing surface, the trailing surface having an inner portion that slopes outwardly and downwardly from the body and an outer portion with a raised surface relative to the inner portion;
(d) a head guide and advancement flange discontinuously extending helically about and along said inner surfaces of said main portions and said extended portions of said arms, said head flange having a head anti-splay contour with an upwardly facing head leading surface;
(e) the anti-splay contours of said closure flange and said head flange being complementary and radially interlocking so as to cooperate to prevent splaying of said arms when said flanges are mated and said closure is rotated and advanced into said screw head with the head flange mating with the closure flange between the arm extended portions and guiding the closure into the channel between the arm main portions; the trailing surface raised surface being sized and shaped to be spaced from the head guide and advancement flange during use;
(f) the closure leading surface and the head leading surface cooperating when said flanges are mated and said closure is rotated and advanced into said screw head with the head flange mating with the closure flange between the arm extended portions and guiding the closure into the channel between the arm main portions; and
(g) said extended portions of said arms being separated from said main portions after said closure clamps the rod within a portion of said channel located between said main portions of said arms.

11. The device as set forth in claim 10 wherein:
(a) said closure anti-splay contour includes a lip extending helically along said closure flange;
(b) said head anti-splay contour includes a groove extending helically along said head flange; and
(c) said lip and said groove cooperate to receive said lip in said groove when said closure is advanced into said screw head.

12. The device as set forth in claim 10 wherein:
(a) said closure flange has a closure load flank on a trailing side of said closure flange relative to a clamping direction of movement of said closure within said screw head;
(b) said closure anti-splay contour includes a lip extending helically along said closure load flank of said closure flange;
(c) said head flange has a head load flank on a trailing side of said head flange relative to said clamping direction of movement;
(d) said anchor anti-splay contour includes a groove extending helically along said anchor load flank of said head flange; and
(e) said lip and said groove cooperate to receive said lip in said groove when said closure is advanced into said head.

13. The device as set forth in claim 10 wherein:
(a) said closure includes a break off insertion head adapted to be driven by an insertion tool and to break off at a preselected torque.

14. The device as set forth in claim 10 wherein:
(a) said bone screw is a polyaxial bone screw.

15. The device as set forth in claim 10 wherein:
(a) said bone screw is a fixed headed bone screw.

16. In a spinal implant having a head with a pair of upwardly extended and spaced arms forming a rod receiving channel therebetween that receives a closure; the improvement comprising:
(a) said arms have upwardly extending break off extensions;
(b) the closure has a body and a flange form thereabout with a trailing surface;
(c) said arms and said extensions each have inwardly facing surfaces with discontinuous helically wound flange forms thereon that interlock with the flange form on the closure and allow advancement and transfer of the closure between said extensions and said arms by rotation of the closure; wherein
(d) the closure includes leading and trailing surfaces; the closure trailing surface having an inner portion sloping downwardly from the body and an outer portion with a raised surface forming a lip that remains spaced from the flange forms of the arms and extensions so as to remain unloaded when the flange forms are mated and said closure is rotated and advanced into said screw head and tightened.

17. A device for securing a rod shaped member and comprising:
(a) a receiver having spaced apart arms defining a member receiving channel therebetween, said arms having main portions and extended portions connected to said main portions by weakened regions, said main portions and said extended portions of said arms having inner surfaces;
(b) a closure with a body and sized to be received within said channel to clamp the rod shaped member therein;
(c) a closure guide and advancement flange extending helically about and along said closure body, said closure flange having a closure anti-splay contour with an inner portion that slopes downwardly and outwardly from the body and an outer portion with a raised surface relative to the inner portion; the outer portion raised surface remaining unloaded in use;

(d) a discontinuous receiver guide and advancement flange extending helically about and along said inner surfaces of said main portions and said extended portions of said arms, said receiver flange having a mating receiver anti-splay contour;

(e) the anti-splay contours of said closure flange and said receiver flange being complementary to mate during rotation of the closure relative to the receiver, while radially interlocking, and thereafter cooperatively to prevent splaying of said arms when said closure is advanced into said receiver; said closure being advance-able to lock rod shaped member to said receiver; and (f) said extended portions of said arms guiding the closure into the channel during rotation of the closure into the channel and thereafter being separable from said main portions after said closure clamps the rod shaped member within a portion of said channel defined by said main portions of said arms.

18. In a spinal implant having a head with a pair of upwardly extended and spaced arms forming a rod receiving channel therebetween that receives a closure; the improvement comprising:

(a) the closure has a body and a flange form thereabout with a trailing surface;

(b) said arms have inwardly facing surfaces with discontinuous helically wound flange forms thereon that interlock with the flange form on the closure and allow advancement of the closure along said arms by rotation of the closure; wherein (c) the closure includes leading and trailing surfaces; the extending outwardly and trailing surface having an inner portion sloping downwardly from the body and an outer portion with a raised surface forming a lip that remains spaced from the flange forms of the arms so as to remain unloaded when the closure and arm flange forms are mated and the closure is rotated and advanced into the screw head and tightened.

* * * * *